United States Patent [19]

Genco et al.

[11] Patent Number: 4,741,999
[45] Date of Patent: May 3, 1988

[54] MONOCLONAL ANTIBODIES USEFUL IN THE IDENTIFICATION OF MICROORGANISMS CAUSING PERIODONTAL DISEASE

[75] Inventors: Robert J. Genco, Buffalo; Joseph J. Zambon, Williamsville; Lars A. Christersson, Snyder; Mirdza E. Neiders, Amherst, all of N.Y.

[73] Assignee: The Research Foundation of State University of New York, Albany, N.Y.

[21] Appl. No.: 833,856

[22] Filed: Feb. 26, 1986

[51] Int. Cl.⁴ .................. C12N 5/00; C12N 15/00; G01N 33/569; G01N 33/577
[52] U.S. Cl. .................. 435/7; 435/172.2; 435/240.27; 435/948; 436/519; 436/548; 530/387; 530/808; 935/110
[58] Field of Search ............ 435/7, 172.2, 240, 948; 436/519, 548; 935/110; 530/387, 808

[56] References Cited

U.S. PATENT DOCUMENTS

| | | | |
|---|---|---|---|
| 4,067,959 | 1/1978 | Bolz | 424/1 |
| 4,185,084 | 6/1980 | Mochida et al. | 424/1 |
| 4,376,110 | 3/1983 | David et al. | 436/513 |
| 4,379,135 | 4/1983 | Sasaki et al. | 436/536 |
| 4,421,860 | 12/1983 | Elings et al. | 436/518 |
| 4,486,530 | 12/1984 | David et al. | 435/7 |
| 4,487,839 | 12/1984 | Kamentsky | 436/528 |

OTHER PUBLICATIONS

R. C. Nowinski et al, *Science*, 219, 637–644, 1983.

*Primary Examiner*—Sidney Marantz
*Assistant Examiner*—David A. Saunders
*Attorney, Agent, or Firm*—Donald C. Studley; Michael L. Dunn

[57] ABSTRACT

*Actinobacillus actinomycetemcomitans* has frequently been implicated in juvenile periodontitis. The present monoclonal antibodies are specific to *Actinobacillus actinomycetemcomitans*. The present monoclonal antibodies are typically employed as reagents which include an inert carrier, preferably a liquid, such as buffered saline solution and a preservative. The carrier compositions are suitably selected to provide for the proper dispersal of bacteria, and to preserve the integrity of antigens and supplemental structures. The selection of the proper carrier is especially important in the detection in mixtures which include bacteria which produce large amounts of autolytic enzymes such as *B. gingivalis*. The monoclonal antibodies of the present invention are useful in clinical testing and differentiating antigens in the gingival or subgingival sera. The method of testing and differentiating involves the steps of contacting a sample of the bacterial flora from a lesion or other site with a measured amount of monoclonal antibody specific to a single antigen site on *Actinobacillus actinomycetemcomitans* and subsequently measuring the number of antibody-antigen complexes formed.

6 Claims, No Drawings

MONOCLONAL ANTIBODIES USEFUL IN THE IDENTIFICATION OF MICROORGANISMS CAUSING PERIODONTAL DISEASE

This invention was made with government support under National Institutes of Health—Periodontal Disease Clinical Research Center—Grant No. DEO4898.

BACKGROUND AND PRIOR ART

The present invention relates to monoclonal antibodies and antigens, and to the use of such antibodies and antigens in the detection of the presence and concentration of certain specific microorganisms implicated in the etiology of human periodontal diseases. More specifically, the present invention relates to monoclonal antibodies specific to antigens from *Actinobacillus actinomycetemcomitans*. *Actinobacillus actinomycetemcomitans* is generally associated with juvenile periodontitis.

Clinical assays specific to such bacteria in gingival and subgingival dental plaque are useful in the diagnosis of periodontal disease, in evaluating the progress of periodontal therapy, and in determining the status of the patient at subsequent recall examinations. The standard bacteriological techniques presently used to identify such microorganisms are time consuming, expensive, and require a high level of expertise. Further, such tests frequently give results which are not as accurate or as sensitive as desired or required.

Recently, various efforts and proposals have been made to improve or replace standard bacteriological techniques by the utilization of immunodiagnostic assay techniques. Such immuno assay techniques are based upon the formation of a complex between the antigenic substance being assayed and an antibody or antibodies in which one or the other member of the complex is labeled. For example, labeling may be by means of a radioactive element, such as $I^{125}$, (radioimmunoprecipitation assays); a material having fluorescent properties (immunofluorescence assays); enzyme-linked immunoabsorbant assays (ELISA) or (immunoperoxidase assays). The labeled member of the complex facilitates detection and/or qualitative analysis of the complexed labeled antigen or antibody from the uncomplexed antigen or antibody.

In typical competition utilizing immunoassay assay techniques, the antigenic substance in the sample of the fluid being tested competes with a known quantity of labeled antigen for a limited quantity of antibody binding sites. Thus, the amount of labeled antigen bound to the antibody is inversely proportional to the amount of antigen in the sample. In contrast, typical immunometric assays employ a labeled antibody. In such assay, he amount of labeled antibody associated with the complex is directly proportional to the amount of antigenic substance in the fluid sample.

Although immunodiagnostic techniques can be a substantial improvement over previously used bacteriological detection techniques, many further improvements remain to be made. For example, the immunodiagnostic techniques presently in use frequently produce variable results because relatively crude antigens and antibodies are employed. For example, three serotypes of *Actinobacillus actinomycetemcomitans* are known to exist in the oral cavity of man, yet one or more of the serotypes frequently goes undetected using present immunodiagnostic techniques. Similarly, there are at least three serologic variants of *B. gingivalis* in the oral cavity of man and they differ in virulence, hence the identification of the serologic variants of *B. gingivalis* by immunologic means can offer considerable advantages over other methods of detection and quantitations, however, present methods do not allow such distinction to be made. The immunodiagnostic techniques which are currently available for use in the determination of periodontal diseases generally lack accuracy, sensitivity and specificity.

Monoclonal antibodies may be defined as identical proteins produced by known techniques. The basic techniques for producing monoclonal antibodies were developed in the mid-1970's after Kohler and Milstein successfully fused spleen lymphocytes with malignant cells (myelomas) of bone marrow primary tumors [C. Milstein, Sci Am. 243(4): 66–74, (1980)]. Monoclonal antibodies recognize a single specific antigenic determinant (chemical structure). A given antigen may have several determinants. Thus, if monoclonal antibodies alone are utilized, immunodiagnostic tests may lack specificity because the same determinant may be found on different antigens or molecules, or false reading may be made because a single antigen may contain repeating determinants. Conventionally produced antigens typically have multiple determinants. Until the present invention, efforts to solve this problem have been made without a great deal of success. It is highly desirable that monoclonal antibodies be produced that not only have the ability to recognize a desired molecule or structure in a complex, but also have the ability not to recognize the same determinant in an unrelated or undesired complex. The present invention provide a specific antigen for microorganisms which are associated with periodontal diseases and to monoclonal antibodies that recognize only those antigens, and more particularly to monoclonal antibodies that recognize specific species, or strains, of such antigens. Thus the present invention provides a means of substantially improving the accuracy of various immuno-diagnostic assays.

BRIEF DESCRIPTION OF THE INVENTION

Specific microorganisms have been strongly associated in the etiology of human periodontal disease and *Actinobacillus actinomycetemcomitans* has frequently been implicated in juvenile periodontitis. The present monoclonal antibodies are specific to *Actinobacillus actinomycetemcomitans*.

The present monoclonal antibodies are typically employed as reagents which include an inert carrier, preferably a liquid, such as buffered saline solution and a preservative. The carrier compositions are suitably selected to provide for the proper dispersal of bacteria, and to preserve the integrity of antigens and supplemental structures. The selection of the proper carrier is also important in the detection of mixtures which include bacteria which produce large amounts of autolytic enzymes such as *B. gingivalis*.

The monoclonal antibodies of the present invention are useful in clinical testing and differentiating antigens in the gingival or subgingival sera. The method of testing and differentiating involves the steps of contacting a sample of the bacterial flora from a lesion or other site with a measured amount of a monoclonal antibody specific to a single antigen site on *Actinobacillus actinomycetemcomitans* and subsequently measuring the number of antibody-antigen complexes formed.

The monoclonal antibodies useful in the present invention are obtained by the process discussed by Milstein and Kohler and reported in *Nature*, 256, 495–97, 1975. The details of the process are well known in the art. Basically, the process involves injecting a mouse, or other suitable animal, with an immunogen. The animal is subsequently sacrificed and cells taken from its spleen and fused with myeloma cells. The result is a hybrid cell, hybridoma, that reproduces in vitro. The population of hybridomas are screened to isolate individual classes each of which secrete a single antibody specific to the antigen. The individual antibody species obtained in this way are each the product of a single B cell from the immune animal generated in response to a specific antigenic site recognized by the immunogenic substance. The monoclonal bodies selected preferably have a response affinity of at least $10^7$ liters/mole and, more preferably, an affinity of at least $10^9$ liters/mole.

DETAILED DESCRIPTION AND PREFERRED EMBODIMENT OF THE INVENTIONS

Actinobacillus actinomycetemcomitans Antigens

*Actinobacillus actinomycetemcomitans* is an oral gram-negative facultative organism which has been associated with severe oral and nonoral infections. *Actinobacillus actinomycetemcomitans* is commonly isolated from patients with juvenile periodontitis, often isolated from patients with adult periodontitis, but only occasionally isolated and in small numbers from normal juveniles and adults. Its primary oral ecological niche appears to be dental plaque and periodontal pockets.

Studies of the antigenic relationships among human *Actinobacillus actinomycetemcomitans* and other bacteria, including a large battery of oral strains, have shown that there are three types of antigens. First, Actinobacillus-Haemophilus "Cross-reactive" antigens which are shared by *Actinobacillus actinomycetemcomitans* and oral Haemophilus species including *Haemophilus aphrophilus, Haemophilus paraphrophilus,* and *Haemophilus parainfluenzae*. The second set are "Species Specific" antigens which are common to strains of the three serotypes of *Actinobacillus actinomycetemcomitans* of human oral origin, but are *not* shared by other organisms including oral Haemophilus strains and other oral organisms. Thirdly, "Serotype Specific" antigens which are unique to each of the three serotypes of *Actinobacillus actinomycetemcomitans*. There are at least three of the latter antigens, one each for serotype a, b, and c.

In order to function as a viable "Species Specific" antigen, the antigenic determinant must be selectively narrow to differentiate *Actinobacillus actinomycetemcomitans* but sufficiently broad to include all serotypes. Heretofore, no viable "Species Specific" antigen has been found. The presently discovered antigens and corresponding monoclonal antibodies allow specific identifications of any of the serotypes of *Actinobacillus actinomycetemcomitans* in samples taken from human periodontal lesions or from lesions taken from elsewhere in the body where such microorganisms may be implicated.

Antibodies

BALB/c mice were immunized with formalized whole cells of *Actinobacillus actinomycetemcomitans* serotype b. In accord with the prior art, the spleens were removed and the cells therefrom were fused to SP-2 myeloma cells using polyethylene glycol, (PEG-1000). The desired hybrid cells were selected by adding hypozanthine-aminopterin-thymidine to the medium. The surviving cells in individual wells of microtiter plates were tested for antibody production and those found positive to the immunizing strain were cloned and retested. One clonal isolate, Clone BAA-24, reactive with antigens 15K and 19K, was found to react specifically with *Actinobacillus actinomycetemcomitans* serotypes a, b or c, but not with a battery of other test organisms likely to be found in samples from periodontal lesions or other sites. Hence, the 15K/19K antigen is a "species-specific" antigen. Another clone, BAA-1 reacts with antigens 97K–120K, and reacts with *Actinobacillus actinomycetemcomitans* serotypes b and c. Clones BAA-24, BAA-1 and BAA-3 do not react with oral Haemophili or a large battery of other microorganisms. These microorganisms tested for specificity include both gram-negative and gram-positive oral microorganisms.

Clones BAA-24, BAA-1 and BAA-3 were inoculated into pristane-treated mice for production of ascites tumors. The ascites fluids were harvested and tested again by ELISA, immunoblot, and Western Blot immunoelectrophoresis procedures. The results indicate that Clone BAA-24 produced antibodies which react only with species specific serotype common antigens of human *Actinobacillus actinomycetemcomitans* of 15K and 19K molecular weights. The results also showed that Clone BAA-1 produced antibodies which react only with an antigen in the 97102K range which is shared by serotypes a and b of *Actinobacillus actinomycetemcomitans*. Further, the results indicate that Clone BAA-3 produced antibodies which react only with a 63K antigen which is shared by serotypes b and c of *Actinobacillus actinomycetemcomitans*. Using these reagents singly or in combinations in various assays including slide immunofluorescence and cytofluorograph immunofluorescence, ELISA, antigen capture ELISA and fluorescent-ELISA, immunoprecipitation, immunoblot and Western blot, and radioimmunoassay, it is possible to specifically detect and quantitate specific strains of *Actinobacillus actinomycetemcomitans* from samples of dental plaque taken from periodontal lesions and other sites in human patients.

Monoclonal antibodies, Clones BAA-24, BAA-1 and BAA-3, are presently registered with In Vitro International, Inc. 7885 Jackson Road, Ann Arbor, MI.

Testing

The monoclonal antibodies of the present invention have been tested in a series of immunologic assays and have shown to be specific for the detection of organisms to which they are directed. For example, Clone BAA-24 has been used in ELISA and immunofluorescence assays which allows detection of *Actinobacillus actinomycetemcomitans* in the presence of a large number of other organisms. The sensitivity and specificity of these assays in comparison to bacterial culture have been assessed and found to be adequate for detection of numbers of organisms. For example, $10^6$ *Actinobacillus actinomycetemcomitans* are often recoverable from lesions of juvenile periodontitis patients at such level is readily detected by immunofluorescence and ELISA.

Immunofluorescence Microscopy

Clinical studies have been performed comparing the use of monoclonal antibodies to *Actinobacillus actinomycetemcomitans* with bacterial culture of these microorganisms. Forty subjects were examined for *Actinobacillus actinomycetemcomitans including 10 normal adults, 10 normal juveniles, 10 adult periodontitis patients, and 10 localized juvenile periodontitis patients. As seen in Table 1, immunofluorescence microscopy using monoclonal antibody Clone BAA-24 was more likely to detect Actinobacillus actinomycetemcomitans than bacterial culture on selective or nonselective media, especially when this microorganism was present in small numbers in subgingival dental plaque. This monoclonal antibody detected the microorganism in many subgingival plaque samples in adult periodontitis patients that could not be seen by culture on nonselective media. The present antibody reagent could detect the microorganism in localized juvenile periodontitis patients in 7% more sites compared to selective media and 16% more sites compared to nonselective media.

TABLE 1

Presence of A. Actinomycetemcomitans in Subgingival Plaque

| Subject Group | Subjects Examined | Sites[a] Examined | Culture Non-Selective Media | Culture Selective Media | Immunofluorescence Monoclonal Antibody (BAA-24) |
|---|---|---|---|---|---|
| Normal Adults | 10 | 60 | 1(1) | 1(1) | 1(2) |
| Normal Juveniles | 10 | 60 | 0 | 1(1) | 1(2) |
| Adult Periodontitis Patients | 10 | 60 | 3(5)[b] | 6(10)[b] | 6(10)[b] |
| Localized Juvenile Periodontitis Patients | 10 | 60 | 8(14)[c] | 14(23)[c] | 18(30)[c] |
| Total | 40 | 240 | 12(5) | 22(9) | 26(11) |

[a]Sites examined were 16M, 21D, 26M, 36M, 41D and 46M; none of the sites was periodontally diseased in normal adults and normal juveniles, 55% of the sites were diseased in adult periodontitis patients, and 25% of the sites were diseased in localized juvenile periodontitis patients.
[b]Twenty-one percent of the periodontally diseased sites and 13% of the periodontally healthy sites were positive for A. actinomycetemcomitans by either technique.
[c]One hundred percent of the periodontally diseased sites and 9% of the periodontally healthy sites were positive for A. actinomycetemcomitans by either technique.

Examination of sensitivity and specificity values demonstrate that monoclonal antibody exhibits 90% sensitivity and 88% specificity compared to culture of A. actinomycetemcomitans on nonselective blood agar media, and also exhibits 82% sensitivity and 92% specificity compared to culture on selective media.

Indirect immunofluorescence microscopy using monoclonal antibody specific to Actinobacillus actinomycetemcomitans can be diagnostic for certain types of periodontal disease. Detection of A. Actinomycetemcomitans by monoclonal antibodies in immunofluorescence slide tests at proportions greater than 12% of the total bacterial cell count from dental plaque sample is correlated with a 100% probability of that patient having localized juvenile periodontitis. That is, when a patient demonstrates greater than 12% A. actinomycetemcomitans in a pooled subgingival plaque sample, then the likelihood of that patient having localized juvenile periodontitis is 100%.

The sensitivity of the immunofluorescence assays is great since theoretically a single cell can be detected among thousands of others given sufficient intensity of staining, and characteristic morphology. However, the slide immunofluorescence assays require laborious visual microscopic inspection of the specimens by a highly trained person. Automation of immunofluorescence using a Cytofluorograph, a product of Ortho Instruments, Westwood, Mass., is preferably used, resulting in a more objective, rapid, enumeration of the organisms, however, the sensitivity is not as great with the slide immunofluorescence assay.

Enzyme-linked Immunosorbent Assays

The following is a flow sheet showing the procedure used in the ELISA assay:

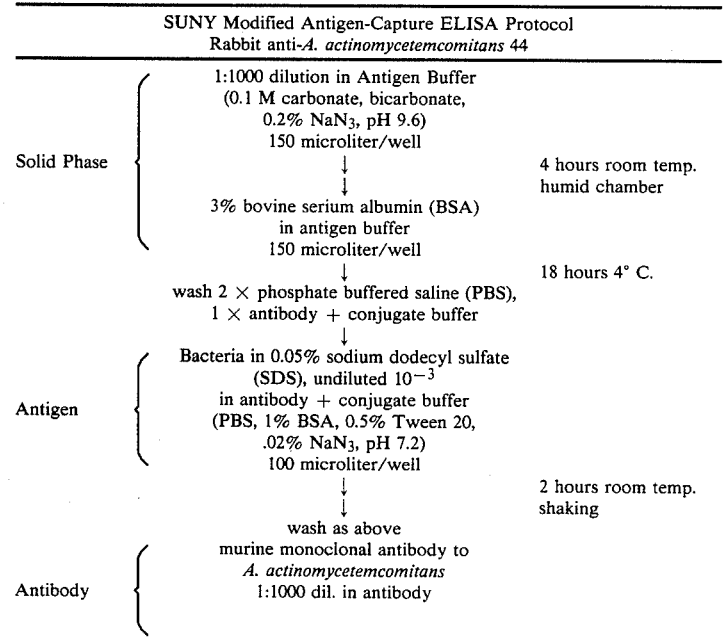

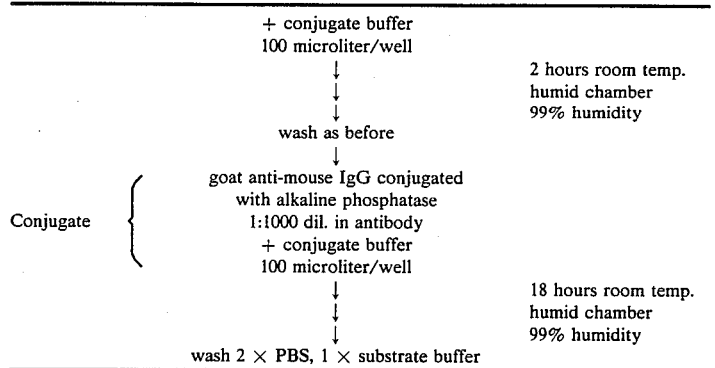

The sensitivity of the ELISA assay may be increased to determine microorganisms in the range of $10^5$ organisms per ml using several modifications of standard assays. Such modifications are:

1. the bacterium are lysed using 0.05% sodium dodecyl sulfate (SDS) to release antigens in soluble form. The soluble antigens are assays by using ELISA, F-ELISA or immunoblot. (This treatment was found to increase the sensitivity 100 fold, increasing the minimum levels for detection of organisms from one million to one thousand per ml.

2. The ELISA and F-ELISA assays are carried out using the "antigen capture" method whereby polyclonal antibody (or another monoclonal antibody) monospecific to the bacterium is absorbed to a well, the antigen is added, and then antibody to the monoclonal antibody (or a second monoclonal antibody if monoclonal antibody is used in the first step) which is conjugated with alkaline phosphatase. The sensitivity of detection is in the range of $10^4$ organisms/ml.

3. In the use of the fluorescent ELISA assay the light adsorbing ligand 2-naphtoyltrifluoroacetone is added and the sensitivity is increased approximately another tenfold by monitoring the production of a fluorescent product in a fluorescent ELISA reader.

4. The use of multiple steps for the detection including the use of avidin or Streptavidin and biotin; "multiple layered sandwiches" using goat anti-mouse IgG subclass sera, and rabbit anti-goat sera, which is conjugated with alkaline phosphatase.

These modifications are useful to increase the sensitivity of the assays which may be necessary for use where few cells are available for sampling, such as after therapy or in the saliva. After therapy for example, there are often $10^6$ organisms recoverable from a lesion. If *A. actinomycetemcomitans* are present at 1% of the total cell population, this requires a sensitivity of approximately $10^4$ cells per ml for accurate determination.

The labeled monoclonal antibodies of the present invention may be provided with the same labels used in the immunometric assays. Among those are fluorogenic labels for detection by fluorimetry as described in U.S. Pat. No. 3,940,475, enzymatic markers as described in U.S. Pat. No. 3,645,090, or radioisotopes as described by Hunter and Greenwood, *Nature* 144, 945, 1962.

The present invention contemplates the use of various test procedure known in the art to determine the presence of bound antibodies in fluids. Such tests include, utilization of plastic surfaces, such as polyvinyl chloride, polystyrene, glass surfaces, and nitrocellulose on which the antigen is coated.

The present antibodies may suitably and preferably be utilized with other antibodies in a monoclonal antibody reagent useful in determining periodontopathogens. For example, *Actinobacillus actinomycetemcomitans* is generally associated with juvenile periodontitis and *Bacteroides gingivalis* is generally associated with adult periodontitis, a preferred method would be to test for both pathogens in each patient.

Sampling Kit

For clinical use of the monoclonal antibodies, in immunologic diagnosis of periodontal organisms, a testing means in the form of a kit may be used to provide a convenient, easy to use method of sampling the subgingival flora, and an effective means of transporting the sample to a reference library where the assays would be performed. In order to induce a standardized sample taking procedure clear instructions should be included in the kit. The kit suitably includes paper points 15-20 mm long with a stiff handle. These may be supplied in a sterile packet with instructions to place in a prepared subgingival site for 10 seconds.

An important component of the kit is the transport media (TM). Our studies have shown that antigens of *B. gingivalis* and to some extent *A. actinomycetemcomitans* are destroyed by storing at room temperature in aqueous buffer. A particularly useful TN has been found to consist of from about 0.1 to about 0.2M NaCl, from about 0.01 to 0.03M $NaPO_4$, buffered to a pH of about 7.2 and from about 0.5 to about 3.0% by weight Formalin (v/v). This transport media preserves the antigens for periods of up to six months. This media also favors adequate dispersal of the bacterial mass from the paper points so that unstable suspensions on smears in which clumping and aggregation is minimal can be made on slides for immunofluorescent analysis, or for cytofluorometric analysis. Furthermore, this media allows for solubilization of the organism for ELISA and other assays using 0.05% SDS added to the transport media described above.

Modifications of the present invention will be apparent to those skilled in the art. It is, therefore, intended that the present invention be limited only by the scope of the following claims.

What is claimed is:

1. A monoclonal antibody reagent useful in determining the presence of pathogens containing at least one monoclonal antibody species specific to the microorganism *Actinobacillus actinomycetemcomitans*.

2. Monoclonal antibodies species specific to microorganism *Actinobacillus actinomycetemcomitans*.

3. A method of determining the presence of *Actinobacillus actinomycetemcomitans* in a gingival fluid comprising the steps of:
   (a) contacting a selected antigenic substance from said pathogens with a monoclonal antibody species specific to said pathogen to form a complex of said antigenic substance and said monoclonal antibody, and
   (b) measuring the amount of said complex by determining the amount of antibody in said formed complex.

4. A method of determining the presence of *Actinobacillus actinomycetemcomitans* in a biological fluid comprising the steps of:
   (a) providing an aliquot of the biological fluid to be studied,
   (b) contacting said aliquot with a measured amount of monoclonal antibodies species specific to distinct antigenic determinants on the surface of the cells of *Actinobacillus actinomycetemcomitans*, and
   (c) determining whether any reaction with said antibodies occurs.

5. The method of claim 4 wherein the antibodies are labeled and said labeled antibodies have a predetermined fluorescence response to a given optical stimulation.

6. The method of claim 4 wherein the amount of reaction is determined and the presence of periodontopathogens is quantitatively derived therefrom.

* * * * *